United States Patent
Goldstein

(10) Patent No.: US 10,616,702 B2
(45) Date of Patent: *Apr. 7, 2020

(54) METHOD AND DEVICE FOR AUDIO RECORDING

(71) Applicant: Staton Techiya, LLC, Delray Beach, FL (US)

(72) Inventor: Steven W. Goldstein, Delray Beach, FL (US)

(73) Assignee: Staton Techiya, LLC, Delray Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/260,454

(22) Filed: Jan. 29, 2019

(65) Prior Publication Data

US 2019/0166444 A1    May 30, 2019

Related U.S. Application Data

(60) Continuation of application No. 15/790,771, filed on Oct. 23, 2017, now Pat. No. 10,212,528, which is a
(Continued)

(51) Int. Cl.
*H01L 29/00*    (2006.01)
*H04R 29/00*    (2006.01)
(Continued)

(52) U.S. Cl.
CPC ......... *H04R 29/004* (2013.01); *A61B 5/0205* (2013.01); *A61B 5/1117* (2013.01); *A61B 5/14542* (2013.01); *A61B 5/6817* (2013.01); *G06F 19/00* (2013.01); *G06F 19/36* (2013.01); *G16H 20/10* (2018.01); *G16H 50/20* (2018.01); *G16H 50/30* (2018.01); *H04M 1/65* (2013.01);
(Continued)

(58) Field of Classification Search
CPC ... H04R 25/505; H04R 25/506; H04R 25/502
USPC .................................................. 381/317
See application file for complete search history.

(56) References Cited

U.S. PATENT DOCUMENTS 6,118,878 A    9/2000 Jones
6,754,359 B1    6/2004 Svean et al.
(Continued)

FOREIGN PATENT DOCUMENTS

EP    1640972    3/2006

*Primary Examiner* — Long K Tran
(74) *Attorney, Agent, or Firm* — Akerman LLP; Peter A. Chiabotti; Mammen (Roy) P. Zachariah, Jr.

(57) ABSTRACT

An acquisition system includes a processor, one or more sensors operatively coupled to the processor where the one or more sensors acquire at the ear, on the ear or within an ear canal, one or more of acceleration, blood oxygen saturation, blood pressure or heart-rate, and the one or more sensors configured to monitor a biological state or a physical motion or both for an event. The event can be a detection of a discrepancy when compared with a set of reference data by the one or more sensors or the biological state or the event can be one of a detection of an abrupt movement of a headset operatively coupled to the processor, a change in location of an earpiece operatively coupled the processor, a touching of the headset, a recognizing of a voice command, a starting or ending of a phone call, or a scheduled time.

20 Claims, 11 Drawing Sheets

Related U.S. Application Data continuation of application No. 15/137,730, filed on Apr. 25, 2016, now Pat. No. 9,900,718, which is a continuation of application No. 14/576,236, filed on Dec. 19, 2014, now Pat. No. 9,323,899, which is a continuation of application No. 14/048,324, filed on Oct. 8, 2013, now Pat. No. 8,918,141, which is a division of application No. 13/556,509, filed on Jul. 24, 2012, now Pat. No. 8,582,782, which is a continuation of application No. 12/024,842, filed on Feb. 1, 2008, now Pat. No. 8,254,591.

(60) Provisional application No. 60/887,800, filed on Feb. 1, 2007.

(51) Int. Cl.
    *H04R 25/00*     (2006.01)
    *H04M 1/65*     (2006.01)
    *A61B 5/0205*     (2006.01)
    *A61B 5/11*     (2006.01)
    *A61B 5/145*     (2006.01)
    *A61B 5/00*     (2006.01)
    *G06F 19/00*     (2018.01)
    *H04R 1/10*     (2006.01)
    *G16H 50/30*     (2018.01)
    *G16H 50/20*     (2018.01)
    *G16H 20/10*     (2018.01)
    *A61B 5/021*     (2006.01)
    *A61B 5/024*     (2006.01)

(52) U.S. Cl.
    CPC ........... *H04R 1/1091* (2013.01); *H04R 25/70* (2013.01); *A61B 5/021* (2013.01); *A61B 5/024* (2013.01); *H04R 2201/109* (2013.01); *H04R 2410/05* (2013.01); *H04R 2499/11* (2013.01)

(56) References Cited

U.S. PATENT DOCUMENTS

| | | | |
|---|---|---|---|
| 7,502,484 B2 | 3/2009 | Ngia et al. | |
| 7,707,268 B2 | 4/2010 | Saito et al. | |
| 7,908,617 B2 | 3/2011 | Kimura | |
| 8,718,295 B2 | 5/2014 | Sung et al. | |
| 9,323,899 B2* | 4/2016 | Goldstein | H04R 25/70 |
| 9,900,718 B2* | 2/2018 | Goldstein | H04R 25/70 |
| 10,212,528 B2* | 2/2019 | Goldstein | H04R 25/70 |
| 2001/0046304 A1 | 11/2001 | Rast | |
| 2002/0143242 A1* | 10/2002 | Nemirovski | H04B 1/3877 600/300 |
| 2003/0193426 A1* | 10/2003 | Vidal | G08C 17/02 341/176 |
| 2004/0148632 A1* | 7/2004 | Park | H04N 5/44582 725/81 |
| 2005/0060232 A1* | 3/2005 | Maggio | G06Q 30/02 705/14.19 |
| 2006/0262938 A1 | 11/2006 | Gauger et al. | |
| 2008/0101638 A1 | 5/2008 | Ziller | |
| 2008/0130906 A1 | 6/2008 | Goldstein | |
| 2009/0105605 A1 | 4/2009 | Abreu | |
| 2011/0293105 A1 | 12/2011 | Arie | |
| 2012/0257764 A1 | 10/2012 | Sung | |
| 2014/0062678 A1* | 3/2014 | de Clercq | G05B 15/02 340/12.5 |
| 2015/0094914 A1* | 4/2015 | Abreu | B60H 1/00742 701/41 |

* cited by examiner

METHOD AND DEVICE FOR AUDIO RECORDING

CROSS-REFERENCE TO RELATED APPLICATION(S)

This application is a continuation of U.S. patent application Ser. No. 15/790,771, filed on Oct. 23, 2017, which is a continuation of U.S. patent application Ser. No. 15/137,730, filed on Apr. 25, 2016, now U.S. Pat. No. 9,900,718, which is a continuation of U.S. patent application Ser. No. 14/576,236, filed Dec. 19, 2014, now U.S. Pat. No. 9,323,899, which is a continuation of U.S. patent application Ser. No. 14/048,324, filed on Oct. 8, 2013, now U.S. Pat. No. 8,918,141, which is a divisional of U.S. patent application Ser. No. 13/556,509, filed on Jul. 24, 2012, now U.S. Pat. No. 8,582,782, which is a continuation of and claims priority to U.S. patent application Ser. No. 12/024,842 filed on Feb. 1, 2008, now U.S. Pat. No. 8,254,591, which claims the benefit of U.S. Provisional Patent Application Ser. No. 60/887,800, filed on Feb. 1, 2007, all of which are herein incorporated by reference in their entireties.

FIELD OF THE INVENTION

The present invention is generally directed to the detection and recording of acoustic events, and in particular, though not exclusively, to the detection and recording of acoustic events as measured by an earpiece.

BACKGROUND OF THE INVENTION

The human auditory system has been increasingly stressed to tolerate high noise and sound levels. However, excessive high level exposure over long durations can damage hearing. Moreover, a user's attention to sounds within the environment can be compromised when media devices such as music players, cell phones, and Bluetooth™ earpieces deliver audio to the ear.

In industrial environments where noise is frequently present, workers can be subject to loud excessive noises over long periods of time in addition to the sounds presented by the media devices. Although earplugs help suppress the noise and mitigate the physiological and psychological effects of the noise on the workers, there are few accurate indications of the noise exposure to which the workers are subjected.

A need therefore can be appreciated for assessing sound exposure levels in various environmental settings.

SUMMARY

Embodiments in accordance with the present invention provide a method and device for audio recording.

At least one exemplary embodiment is directed to the detection and recording of acoustic events, and in at least one exemplary embodiment is further directed to a device for sound reproduction, sound recording, audio forensics and audio communications using earpieces.

At least one exemplary embodiment is directed to a multiple earpiece device (e.g., a headset) which can include a left earpiece, a right earpiece, a memory and a processor. The left earpiece can include a left Ambient Sound Microphone (LASM) to capture ambient sound in an environment, and a left Ear Canal Microphone (LECM) to capture internal sound in a left ear canal. The right earpiece can include a right Ambient Sound Microphone (RASM) to capture the ambient sound in the environment and a right Ear Canal Microphone (RECM) to capture internal sound in a right ear canal. The internal sound can be an ambient sound, speech, or audio content portion resident in the ear canal. The memory (e.g., RAM) can record a history (e.g., Sound pressure level (SPL) as a function of time) of the ambient sound and the internal sound, and the processor can save a recent portion of the history responsive to an event. The event can be a touching of the headset, a recognizing of a voice command, a starting or ending of a phone call, or a scheduled time. In one configuration, the processor can trigger the event responsive to detecting an abrupt movement of the headset, or a change in location of the earpiece.

The memory can include a data buffer to temporarily capture the ambient sound and the internal sound, and a storage memory to save from the data buffer the recent portion of the history in a compressed data format responsive to a directive by the processor. In one configuration, the data buffer can be a circular buffer that temporarily stores the ambient sound and the internal sound at a current time point to a previous time point. The processor can save a last two minutes of the history, and audibly present the last two minutes responsive to a user request. The history can be at least one among a conversation, a voice mail, and an audio recording. Additionally the history can record data (e.g., SPL values) from both earpieces. Also note that in at least one exemplary embodiment a single earpiece can be used. The earpiece can include an audio interface communicatively coupled to the processor to deliver audio content by way of a left Ear Canal Receiver (LECR) and a right ECR, wherein the memory records a history of the audio content with the residual sound and the internal sound. In one arrangement, at least a portion of the left earpiece and a portion of the right earpiece can constitute a microphone array, and the processor can increase a signal to noise ratio of the audio content with respect to the ambient sound using the microphone array. The processor can binaurally record the ambient sound and the internal sound from the left earpiece and the right earpiece.

At least one further exemplary embodiment is directed to an earpiece at least partially occluding an ear canal, which can include an Ambient Sound Microphone (ASM) to capture ambient sound in an environment, an Ear Canal Microphone (ECM) to capture internal sound in the ear canal, a memory to record a history of the ambient sound and the internal sound, and a processor operatively coupled to the ASM, the ECM and the memory to save a recent portion of the history responsive to an event. The event can be a touching of the headset, a recognizing of a voice command, a starting or ending of a phone call, a scheduled time, or an abrupt movement of the headset. The processor can save the history of at least one among a conversation, a voice mail, and an audio recording responsive to the event. In another arrangement, the processor can monitor the ambient sound for a Sound Pressure Level (SPL) change, and in response to detecting the SPL change commit the history to the memory.

At least one further exemplary embodiment is directed to an earpiece at least partially occluding an ear canal, which can include an Ambient Sound Microphone (ASM) to capture ambient sound in an environment, an Ear Canal Microphone (ECM) to capture internal sound in the ear canal, an Ear Canal Receiver (ECR) to deliver audio content to an ear canal, a memory to record a history of the ambient sound, the internal sound, and the audio content, and a processor operatively coupled to the ASM, the ECM and the memory to save a recent portion of the history responsive to an event.

The processor can continually record the history in the memory. The event can be a touching of the headset, a recognizing of a voice command, a starting or ending of a phone call, or an abrupt movement of the headset.

At least one exemplary embodiment is directed to a method for audio recording, which can include the steps of measuring ambient sound in an environment, measuring internal sound in an ear canal, continually recording a history of the ambient sound and the internal sound, and saving a recent portion of the history responsive to detecting an event. The step of continually recording can include temporarily saving the history to a circular data buffer based on a chosen data management scheme (e.g., first-in first-out (FIFO)). A time stamp, a location, and the earpiece (e.g., if there are multiple earpieces) can also be recorded with the history. The method can include recording an audio content delivered to the ear canal with the history in a compressed data format. The event can be a touching of the headset, a recognizing of a voice command, a starting or ending of a phone call, an abrupt movement of the headset, or a scheduled time.

At least one further exemplary embodiment is directed to a method for audio recording, which can include measuring ambient sound in an environment, measuring internal sound in an ear canal, measuring audio content delivered to the ear canal, continually recording a history of the ambient sound, the internal sound and the audio content, and saving a recent portion of the history responsive to detecting an event that is at least one among a touching of the headset, a recognizing of a voice command, a starting or ending of a phone call, or an abrupt movement of the headset. The method can further include data compressing the recent portion of the history in a memory, and issuing a warning message to inform a user when a remaining memory receiving the recent portion of the history is below a predetermined value. The recent portion of the history can be audibly presented responsive to a user request.

DETAILED DESCRIPTION

Figure 1:
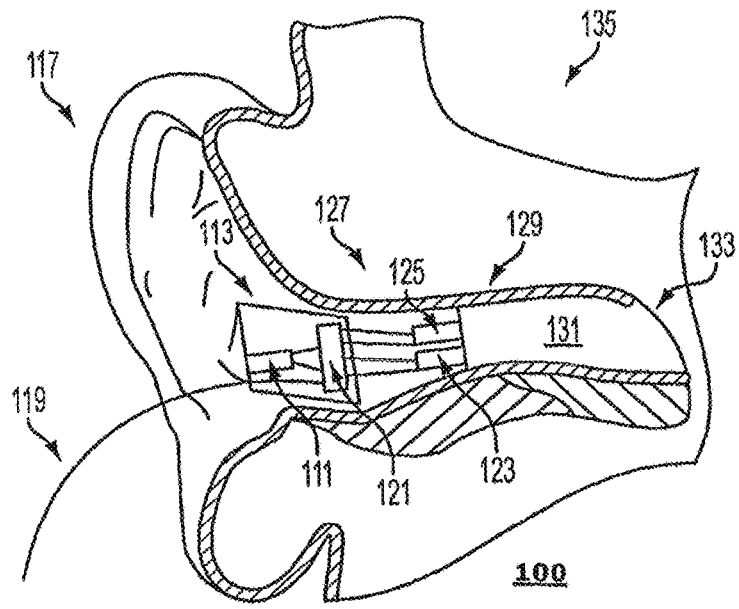
FIG. 1 is a pictorial diagram of an earpiece in accordance with at least one exemplary embodiment.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

At least one exemplary embodiment of the invention is directed to an earpiece for ambient sound monitoring and warning detection. Reference is made to FIG. 1 in which an earpiece device, generally indicated as earpiece 100, is constructed and operates in accordance with at least one exemplary embodiment of the invention. As illustrated, earpiece 100 depicts an electro-acoustical assembly 113 for an in-the-ear acoustic assembly, as it would typically be placed in the ear canal 131 of a user 135. The earpiece 100 can be an in the ear earpiece, behind the ear earpiece, receiver in the ear, open-fit device, or any other suitable earpiece type. The earpiece 100 can be partially or fully occluded in the ear canal 131, and is suitable for use with users having healthy or abnormal auditory functioning.

Earpiece 100 includes an Ambient Sound Microphone (ASM) 111 to capture ambient sound, an Ear Canal Receiver (ECR) 125 to deliver audio to an ear canal 131, and an Ear Canal Microphone (ECM) 123 to assess a sound exposure level within the ear canal 131. The earpiece 100 can partially or fully occlude the ear canal 131 to provide various degrees of acoustic isolation. The assembly is designed to be inserted into the users ear canal 131, and to form an acoustic seal with the walls 129 of the ear canal at a location 127 between the entrance 117 to the ear canal 131 and the tympanic membrane (or ear drum) 133. Such a seal is typically achieved by means of a soft and compliant housing of assembly 113. Such a seal creates a closed cavity 131 of approximately 5 cc between the in-ear assembly 113 and the tympanic membrane 133. As a result of this seal, the ECR (speaker) 125 is able to generate a full range bass response when reproducing sounds for the user. This seal also serves to significantly reduce the sound pressure level at the user's eardrum 133 resulting from the sound field at the entrance to the ear canal 131. This seal is also a basis for a sound isolating performance of the electro-acoustic assembly 113.

Located adjacent to the ECR 125, is the ECM 123, which is acoustically coupled to the (closed) ear canal cavity 131. One of its functions is that of measuring the sound pressure level in the ear canal cavity 131 as a part of testing the hearing acuity of the user as well as confirming the integrity of the acoustic seal and the working condition of the earpiece 100. In one arrangement, the ASM 111 can be housed in the assembly 113 to monitor sound pressure at the entrance to the occluded or partially occluded ear canal 131. All transducers shown can receive or transmit audio signals to a processor 121 that undertakes audio signal processing and provides a transceiver for audio via the wired or wireless communication path 119.

Figure 2:
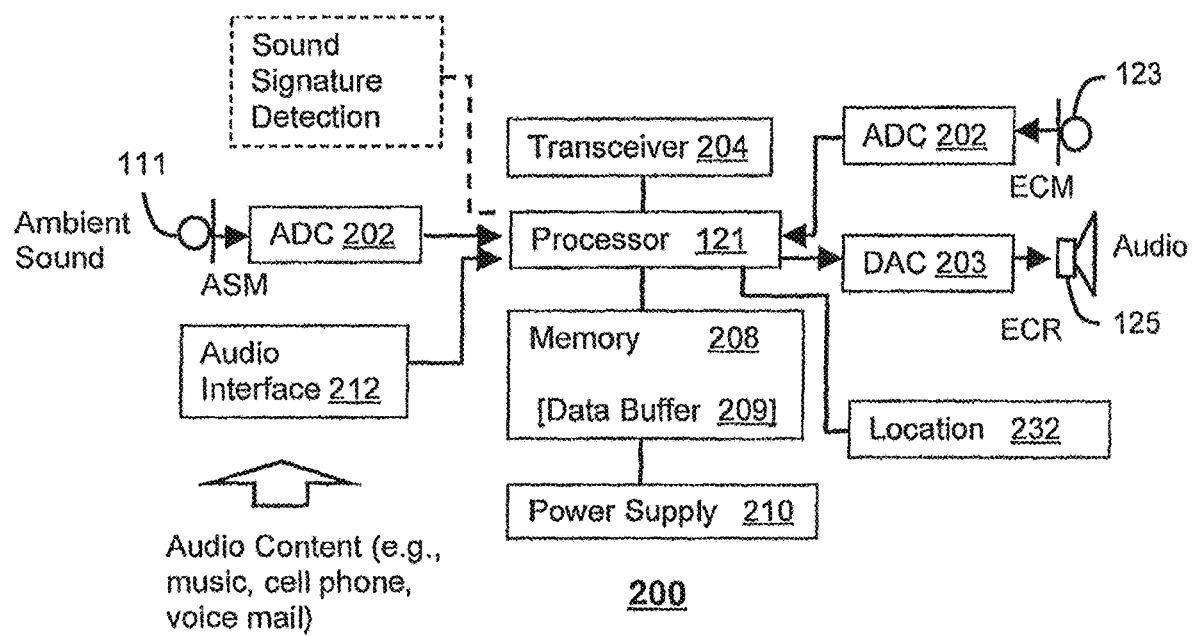
FIG. 2 is a block diagram of the earpiece in accordance with at least one exemplary embodiment.

Referring to FIG. 2, a block diagram 200 of the earpiece 100 in accordance with an exemplary embodiment is shown. As illustrated, the earpiece 100 can include the processor 121 operatively coupled to the ASM 111, ECR 125, and ECM 123 via one or more Analog to Digital Converters (ADC) 202 and Digital to Analog Converters (DAC) 203. The processor 121 can utilize computing technologies such as a microprocessor, Application Specific Integrated Chip (ASIC), and/or digital signal processor (DSP) with associated storage memory 208 such as Flash, ROM, RAM, SRAM, DRAM or other memory based technologies for controlling operations of the earpiece device 100. The processor 121 can also include a clock to record a time stamp.

The memory 208 can store program instructions for execution on the processor 121 as well as captured audio processing data. For instance, memory 208 can be off-chip and external to the processor 121, and include a data buffer 209 to temporarily capture the ambient sound and the internal sound as a history, and a storage memory to save from the data buffer the recent portion of the history in a compressed data format responsive to a directive by the processor. The data buffer 209 can be a circular buffer that temporarily stores audio sound at a current time point to a previous time point. It should also be noted that the data buffer 209 can in one configuration reside on the processor 121 to provide high speed data access. The storage memory 208 can be non-volatile memory such as SRAM to store captured or compressed data format.

The earpiece 100 can include an audio interface 212 operatively coupled to the processor 121 to receive audio content, for example from a media player or cell phone, and deliver the audio content to the processor 121. The processor 121 responsive to detecting events can among various operations save the history in the data buffer 209 to the longer term storage memory 208. The processor 121 by way of the ECM 123 can also actively monitor the internal sound exposure level inside the ear canal 131 and adjust the audio to within a safe and subjectively optimized listening level range.

The earpiece 100 can further include a transceiver 204 that can support singly or in combination any number of wireless access technologies including without limitation Bluetooth™, Wireless Fidelity (WiFi), Worldwide Interoperability for Microwave Access (WiMAX), and/or other short or long range communication protocols. The transceiver 204 can also provide support for dynamic downloading over-the-air to the earpiece 100. It should be noted that next generation access technologies can also be applied to the present disclosure.

The location receiver 232 can utilize common technology such as a common GPS (Global Positioning System) receiver that can intercept satellite signals and therefrom determine a location fix of the earpiece 100.

The power supply 210 can utilize common power management technologies such as replaceable batteries, supply regulation technologies, and charging system technologies for supplying energy to the components of the earpiece 100 and to facilitate portable applications. A motor (not shown) can be a single supply motor driver coupled to the power supply 210 to improve sensory input via haptic vibration. As an example, the processor 121 can direct the motor to vibrate responsive to an action, such as a detection of a warning sound or an incoming voice call.

The earpiece 100 can further represent a single operational device or a family of devices configured in a master-slave arrangement, for example, a mobile device and an earpiece. In the latter embodiment, the components of the earpiece 100 can be reused in different form factors for the master and slave devices.

Figure 3:
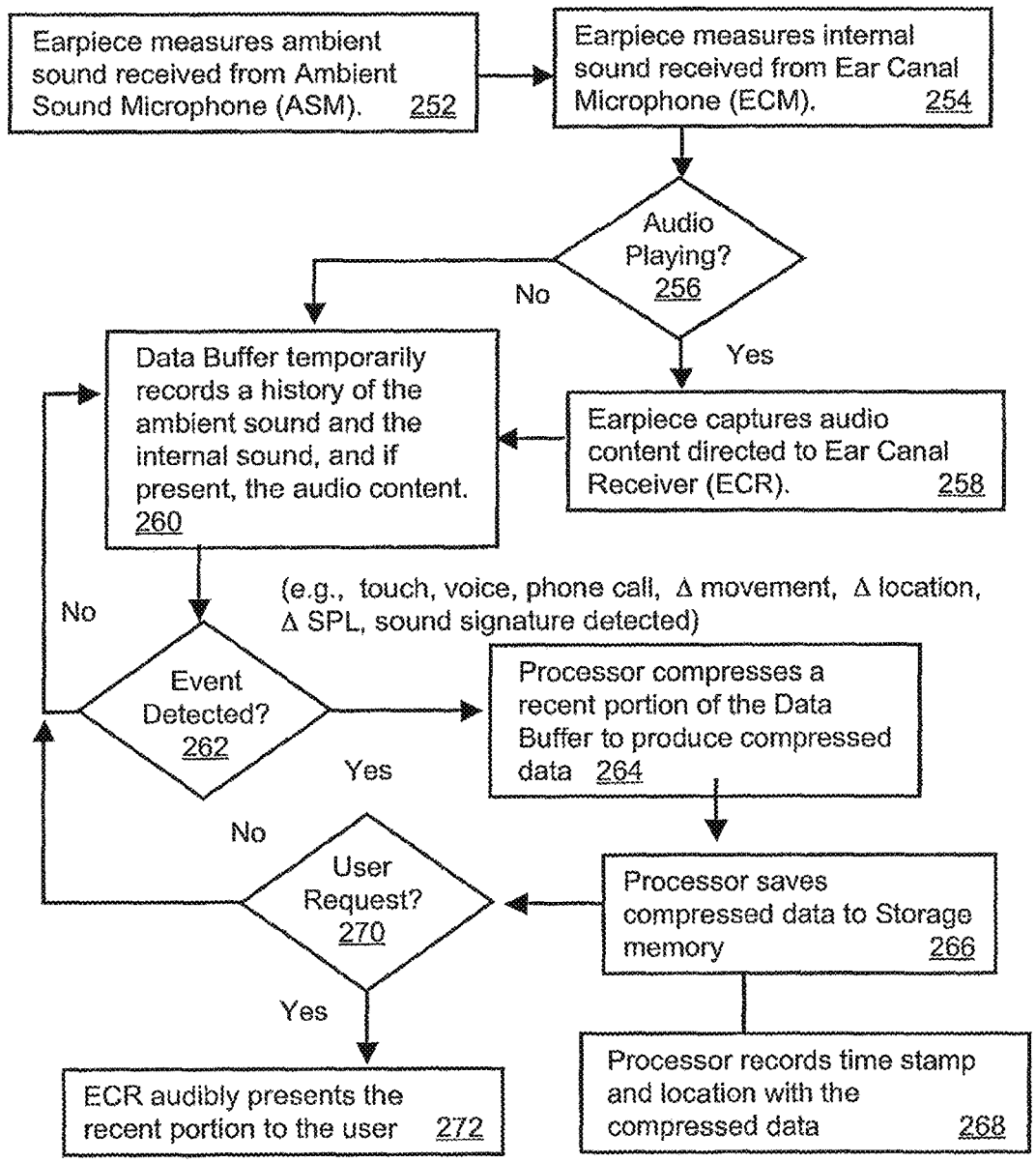
FIG. 3 is a flowchart of a method for audio recording in accordance with at least one exemplary embodiment.

FIG. 3 is a flowchart of a method 250 for audio recording in accordance with an exemplary embodiment. The method 250 can be practiced with more or less than the number of steps shown and is not limited to the order shown. To describe the method 250, reference will be made to components of FIG. 1 and FIG. 2, although it is understood that the method 250 can be implemented in any other manner using other suitable components. The method 250 can be implemented in a single earpiece, a pair of earpieces, headphones, or other suitable headset audio delivery device.

The method 250 can start in a state wherein the earpiece 100 has been inserted and powered on. As shown in step 252, the earpiece 100 can measure ambient sounds in the environment received at the ASM 111. Ambient sounds correspond to sounds within the environment such as the sound of traffic noise, street noise, conversation babble, or any other acoustic sound. Ambient sounds can also correspond to industrial sounds present in an industrial setting, such as factory noise, lifting vehicles, automobiles, and robots to name a few.

Although the earpiece 100 when inserted in the ear can partially occlude the ear canal, the earpiece 100 may not completely attenuate the ambient sound. During the measuring of ambient sounds in the environment, the earpiece 100 can also measure internal sounds, such as ear canal levels, via the ECM 123 as shown in step 254. The passive aspect of the earpiece 100, due to the mechanical and sealing properties, can provide upwards of a 22 dB noise reduction. However, portions of ambient sounds higher than the noise reduction level may still pass through the earpiece 100 into the ear canal thereby producing residual sounds. For instance, high energy low frequency sounds may not be completely attenuated. Accordingly, residual sound may be resident in the ear canal producing internal sounds that can be measured by the ECM 123. Internal sounds can also correspond to spoken voice when the user is speaking or audio content delivered by the ECR 125 to the ear canal 131 by way of the audio interface 212.

If at step 256, audio is playing (e.g., music, cell phone, etc.), the earpiece 100 at step 258 can capture audio content directed to the ECR 125. Portions of the audio content can be saved in the data buffer 209 with the ambient sound and internal sounds. For instance, the audio interface 212 can deliver sound to the occluded ear canal 131 via the ECR 125. The audio interface 212 can receive the audio content from at least one among a portable music player, a cell phone, and a portable communication device. For instance, a user can elect to play music through the earpiece 100 which can be audibly presented to the ear canal 131 for listening. The user can also elect to receive voice communications (e.g., cell phone, voice mail, messaging) via the earpiece 100. The user can receive audio content for voice mail or a phone call directed to the ear canal via the ECR 125.

At step 260, the data buffer 209 temporarily records a history of the ambient sound and the internal sound; and if present, the audio content. The internal sound can correspond to residual ambient sound in the ear canal, speech generated by the user wearing the earpiece 100 when talking, or audio content delivered from the audio interface 212 from a media device (e.g., iPod®, cell phone, radio, etc.). The history can correspond to at least one among a conversation, a voice mail, and an audio recording. For instance, the portions of audio data from a voice mail can be stored for later retrieval (e.g., phone number, address, names, etc.).

Notably, the data buffer 209 stores the ambient sound from the ASM 111 and internal sound from the ECM 123 only temporarily until an event is detected. In one arrangement, the data buffer 209 can temporarily store at least 2 minutes of recording history. The data buffer 209 continually buffers in data while the last data samples in time (unable to be stored in the data buffer 209 due to limited memory) are discarded from the data buffer 209 to make room for the new data. The processor 121 can also interleave the data onto the data buffer 209 during real-time continuous data acquisition.

If at step 262, an event is detected the processor can proceed to save a history of the ambient sound, internal sound, and audio content in the data buffer 209 to the memory 208. An event can correspond to a user event such as a touching of the headset, a recognizing of a voice command, a starting or ending of a phone call, or a scheduled event. The event can also be due to a change in Sound Pressure Level (SPL) or a detected sound signature; that is, a specific sound within the ambient sound (e.g. "horn", "siren", "help"). The processor 121 can monitor the ambient sound for a Sound Pressure Level (SPL) change event, and in response to detecting the SPL change event commits the audio history on the data buffer 209 to the memory 208. For instance, the earpiece 100 can commit recently captured data on the data buffer 209 to the memory 208 responsive to detecting a loud explosion or crashing sound. The earpiece 100 can continue back to step 260 if an event is not detected, while continuing to monitor for events at step 262.

The event can also correspond to an abrupt movement or a change in location of the earpiece 100. For instance, the processor can trigger the event responsive to detecting an abrupt movement of the headset, for instance, due to an accident, or a change in location of the earpiece, for instance, an abrupt aggregated movement. In such regard, the earpiece 100 performs as a black box to record the few minutes prior to an event. Notably, this audio history is available on the data buffer 209 at the time of the event. Moreover, if dual earpieces are used (e.g., headphones), the processor 121 can binaurally record the ambient sound and the internal sound (and, if present, the audio content) from a left earpiece and a right earpiece. The binaural data can be further analyzed to identify a location of sound sources triggering the event.

Upon detecting the event at step 262, the processor 121 can apply data compression techniques to reduce the dimensionality of the data as shown in step 264. The processor 121 can retrieve data from the data buffer 209, compress the data, and store the data in the storage memory 208 as shown in step 266. For instance, the processor 121 can implement a voice coding (vocoder) operation to compress the data from Pulse Code Modulation (PCM) format to a smaller memory footprint format (e.g., EFR723, EFR726, EFR729). If audio content is present, the processor 121 can stream the data from audio interface 212 in an already compressed format (e.g., MP3, AAC, WMA, etc.) Other audio compression techniques can be used for storing the data to the memory 208.

The processor 121 can also time stamp the data (e.g., D/M/Y, hh:mm:ss, etc.) and record a location (e.g., latitude, longitude, elevation, degrees) of the earpiece at the time of the event, as shown in step 268. For instance, in response to an abrupt movement of the earpiece 100 due to an accident, the processor 121 can capture the history of the audio prior to the accident, as well as the time and the location. This information can then be reported to a system that monitors the earpiece 100 for reporting a potential accident or alarming incident. The processor 121, can also tag the data in the storage memory 208 with a filename or header that reflects the condition of the user event. For instance, the header can be saved with the history and include the time stamp, location, and event type (user initiated, abrupt movement, location change, etc.).

If at step 270 a user request (or any other request) is initiated to retrieve stored data, the earpiece 100 can audibly present the recent portion of the history to the user via the ECR 125, as shown in step 272. The recent portion can include any historic audio data previously captured (by way of ASM, ECM, ECR) and stored to the memory 208. Notably, the processor 121 can keep track (e.g., look-up table) of the recent portions stored in the memory 208. For instance, a first entry in the memory 208 can correspond to a recording at 1 PM, and a second entry can correspond to a recording at 1:40 PM. The earpiece 100 can continue back to step 260 if a user request is not received, and continue to monitor for a user request.

The user request can also correspond to a system request to retrieve audio data from the earpiece 100. For instance, the user can subscribe to a service that stores the audio data when memory capacity is reached. Upon the processor determining that memory capacity is full, the earpiece 100 by way of the transceiver 204 can inform the service to retrieve (upload) data from the earpiece. A service provider of the service can then download the data from the earpiece 100 and forensically analyze content within the audio (e.g., spoken commands, passing sounds, voice identification, etc.)

Figure 4:
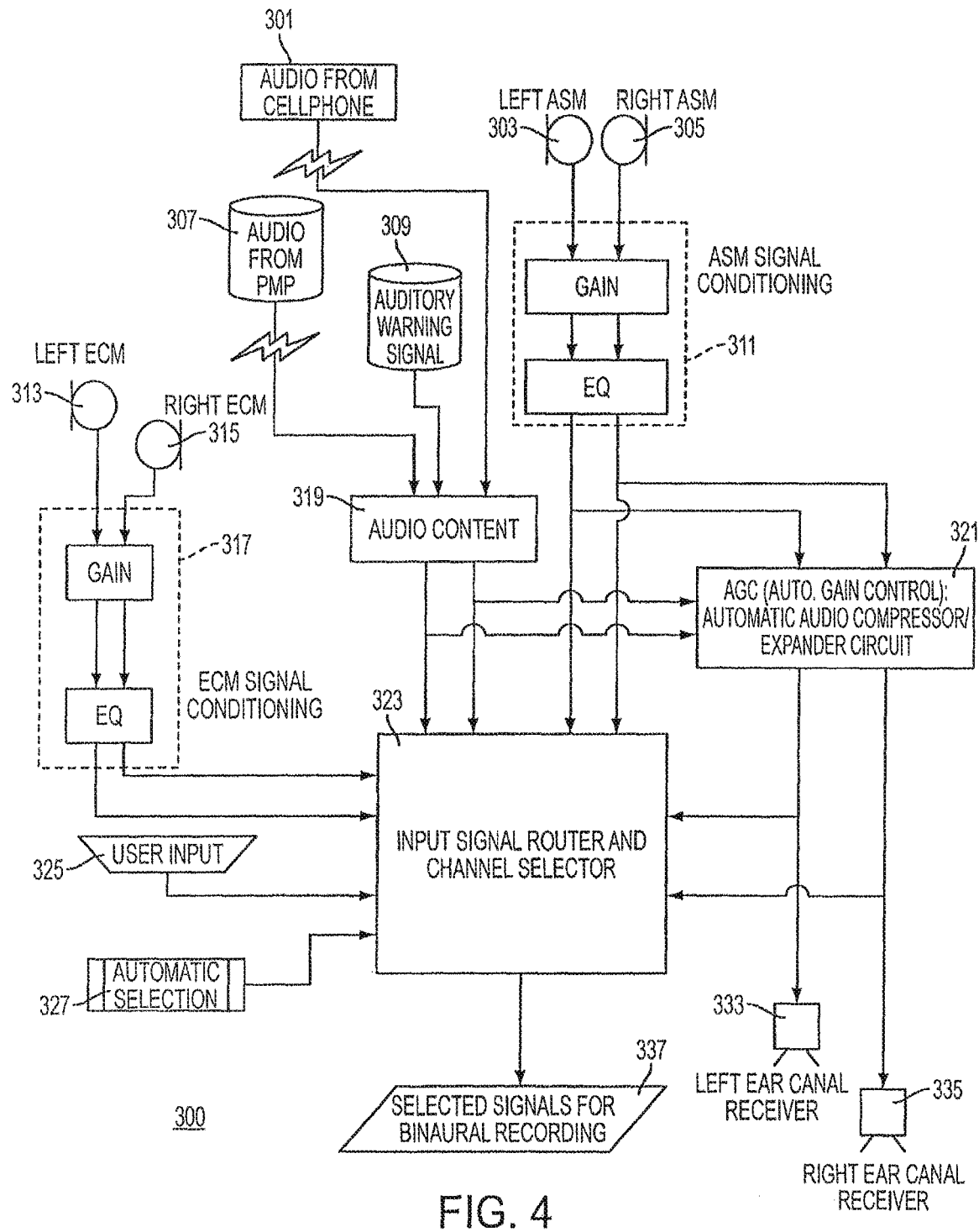
FIG. 4 is a block diagram for audio selection in accordance with at least one exemplary embodiment.

FIG. 4 is a block diagram 300 for audio selection in accordance with an exemplary embodiment. To describe the block diagram 300, reference will be made to components of FIG. 2, although it is understood that the block diagram 300 can be implemented in any other manner using other suitable components. The block diagram 300 can be implemented in a single earpiece, a pair of earpieces, headphones, or other suitable headset audio delivery device.

Block diagram 300 describes an input audio channel selection system to select which audio signals are recorded using an "Always-on" Binaural Recording System (AO-BRS). Input signals to the AOBRS comprise the signal generated by one or both the Ear Canal Microphones (left ECM 313 and right ECM 315), which are processed using gain and equalizer (EQ) circuitry 317 (which may be implemented using analog or digital electronics). Other input signals may comprise one or both Ambient Sound Microphones (left ASM 303 and right ASM 305) from separate left and right headset electroacoustic assemblies, or from the output of multiple ASM signals in the same right headset electroacoustic assembly. The ASM signals are processed using gain and equalizer circuitry 311 (which may be implemented using analog or digital electronics) housed in assembly 113. Audio Content 319 can be recorded during simultaneous reproduction with left and right Ear Canal Receivers 333, 335, via the automatic gain control (AGC) circuitry 321 (which may comprise either or both analog or digital signal processing). Audio Content 319 may be, for example, from a cell-phone 301; a Personal Media Player (PMP) 307; or an auditory warning signal 309 such as a low battery alarm generated by the AOBRS or from a second device such as a second data storage system. The audio signals from circuitry 317, 319, 311, and 321 are selected for recording 337 using the switching assembly 323, and configured either manually with user input system 325 (e.g. using buttons mounted on the electroacoustic headset system) or with automatic selection 327 which may be initiated in response to a specific record start/stop command, for example, generated by the system 449 described in FIG. 6.

Figure 5:
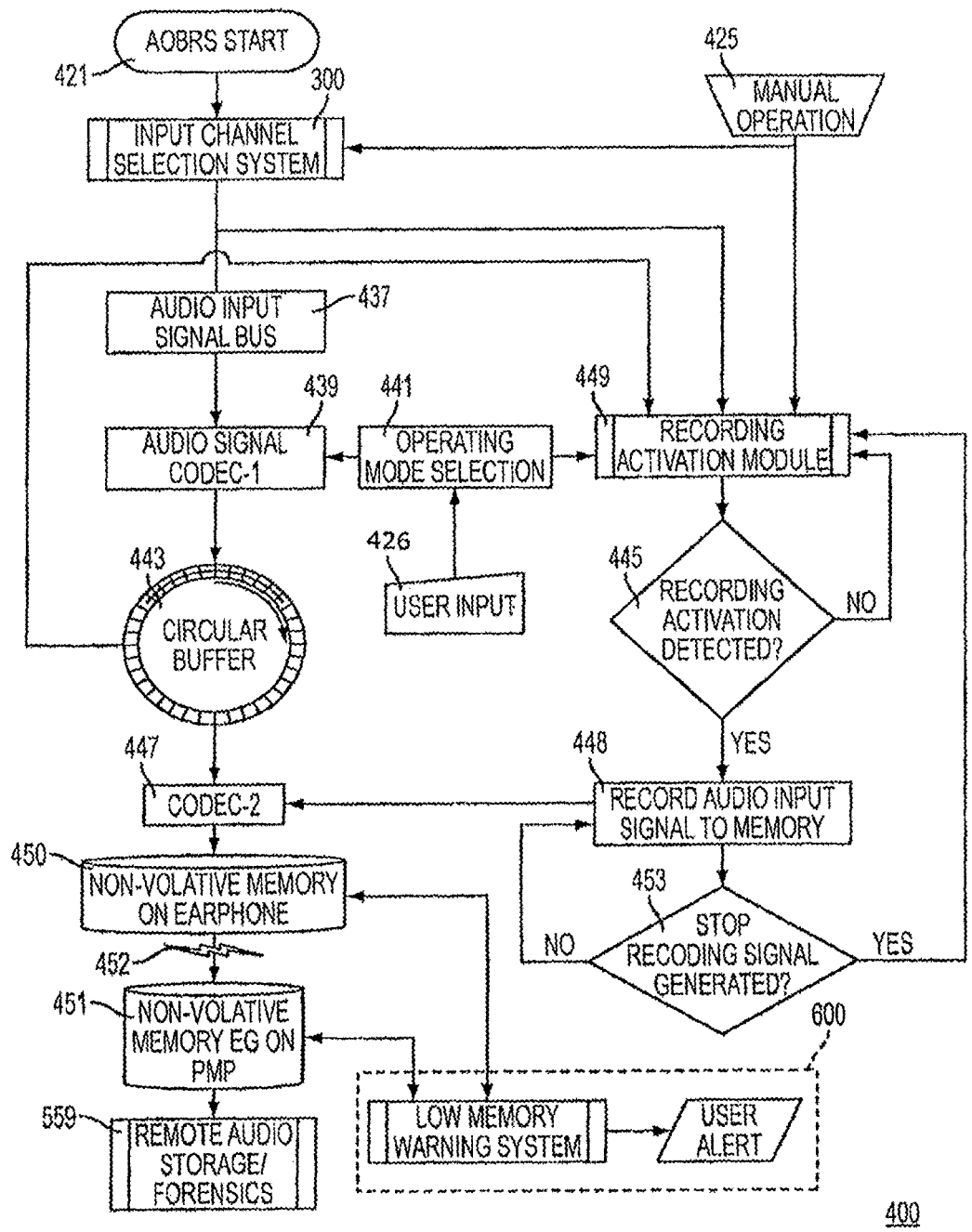
FIG. 5 is a block diagram for always-on binaural recording in accordance with at least one exemplary embodiment.

FIG. 5 is a block diagram 400 for an "Always-On" Binaural Recording System (AOBRS) in accordance with an exemplary embodiment. To describe the block diagram 400, reference will be made to components of FIG. 2, although it is understood that the block diagram 400 can be implemented in any other manner using other suitable components. The block diagram 400 can be implemented in a single earpiece, a pair of earpieces, headphones, or other suitable headset audio delivery device.

Figure 6:
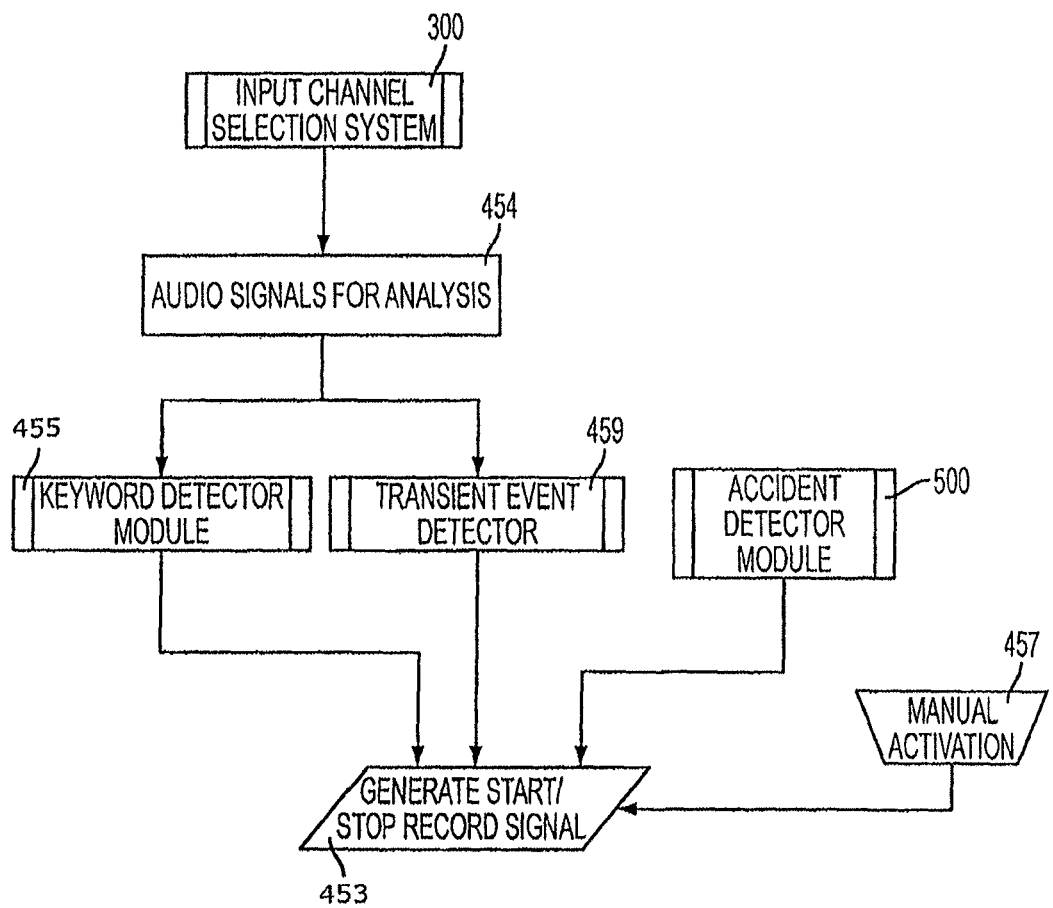
FIG. 6 is a block diagram for activating audio recording in accordance with at least one exemplary embodiment.

Following activation at step 421 and selection (300 shown in FIG. 4) of the audio signals to be recorded (for example, by manual operation 425), the selected audio signals 437 are analyzed by the recording activation circuitry 449 described in FIG. 6. Depending on the operating mode selected 441 (for example, by user input 426), the audio input audio signals 437 are first processed by an optional audio signal CODEC 439, which may reduce the data bit-rate of the signal using either a lossy or lossless data compression system. The audio data is then continuously recorded to a circular data buffer 443 which in the preferred embodiment is housed within the earpiece 100, or on a second device such as a Personal media player (PMP). The circular buffer 443 consists of computer memory, and is a familiar device for those skilled in the art. Following recording activation determined by decision unit 445, the contents of the circular data buffer 443 are recorded to a second non-volatile memory 450, which may be at a compressed data rate using audio signal CODEC 447 (which may use a lossy or loss-less data compression system) receiving recorded audio 448. The recording may continue until a stop recording signal is generated 453. With either a wired or wireless data communication system 452, the contents of the data storage 450 may be stored on a separate data memory device 451, such as a portable hard drive. The remaining data memory of either or both systems 450 and 451 are monitored using a low memory warning system (see 600 FIG. 10), which alert the user when remaining memory is low. A remote audio forensic analysis system 559 described in FIG. 9 can analyze the contents of the first 450 or second 451 audio data storage system, for example, following a detected accident.

FIG. 6 is a block diagram for activating audio recording by recording activation circuitry 449 in accordance with an exemplary embodiment. To describe the block diagram, reference will be made to components of FIG. 2, although it is understood that the block diagram can be implemented in any other manner using other suitable components. The block diagram can be implemented in a single earpiece, a pair of earpieces, headphones, or other suitable headset audio delivery device.

The input audio signal for analysis are selected with the input channel selection system 300 described in FIG. 4. The signals 454 comprise the ASM signals from one or both earphones (though different audio signals may be recorded to data memory for storage). A keyword detector module 455 analyzes the input signals 454 and activates or deactivates recording 453 if specific verbal commands are detected (e.g. "Start", "Stop", which may be in multiple languages). Alternatively or additionally, a method 459 for Transient Event Detection (described in FIG. 7) generates a stop or start signal to the system 300 in response to a detected transient in signal 454 with a particular temporal envelope profile. Alternatively or additionally, an accident detector module 500 (see FIG. 8) generates a stop or start signal to the system 300 in response to a particular user biological state or movement. Alternately or additionally, a stop or start signal 453 is generated to the system 300 in response to a manual user activation 457, such as with a switch mounted on the earphone assembly.

Figure 7:
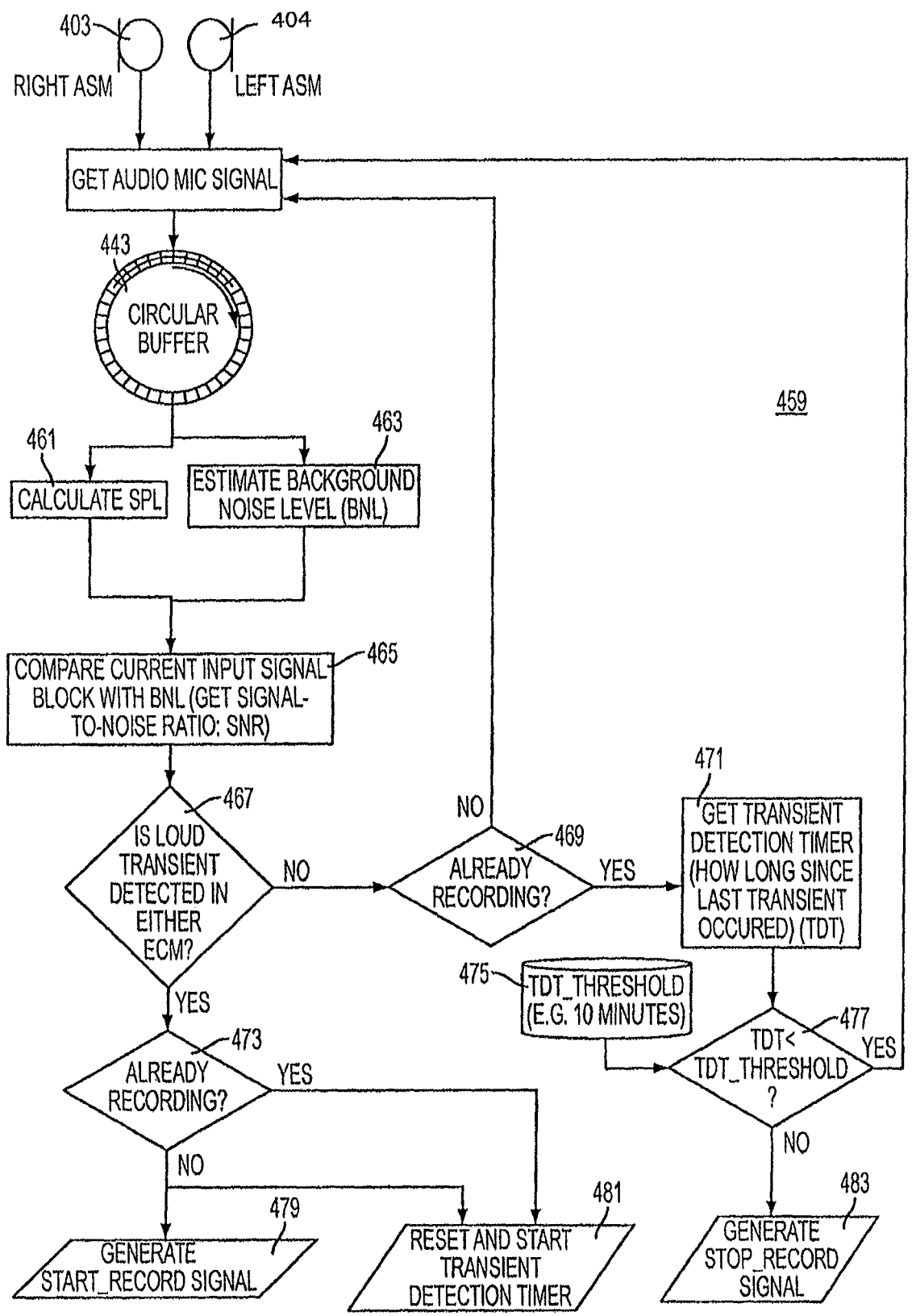
FIG. 7 is a flowchart of a method for transient event detection in accordance with at least one exemplary embodiment.

FIG. 7 is a flowchart further detailing the method 459 for transient event detection in accordance with an exemplary embodiment. The method 459 can include more or less than the number of steps shown and is not limited to the order of the steps. To describe the method 459, reference will be made to components of FIG. 2, although it is understood that the method 459 can be implemented in any other manner using other suitable components. The method 459 can be implemented in a single earpiece, a pair of earpieces, headphones, or other suitable headset audio delivery device.

Transient Event detection generates a stop or start signal to the system 300 in response to a detected transient in either or both the ASM signals 403, 404 (which may be from the same or different earphones). The audio data is continuously recorded to a circular data buffer 443, and a recent history of data samples (e.g. the past 10 ms) is used to estimate the SPL 461 at the entrance to the occluded ear canal 131 (e.g. in dB). The Background Noise Level (BNL) is also estimated at step 463 from a running time-smoothed average of the SPL, which may use circuitry to remove transient peaks in the SPL to calculate the BNL. If the decision unit 467 deems that the difference between the SPL 461 and BNL 463 is less than a predefined amount (which may be determined on a frequency selective basis)—as calculated with unit 465— then the recording is stopped 469 if it is already activated. If the recording is already active, then the Transient Detection Timer (TDT) 471 (which is the time since recording was activated) is compared with a predefined constant 475 using comparator 477, and if the TDT 471 is greater than the threshold 475 then recording is stopped 483. Alternatively, if a loud transient is detected 467, then the TDT clock is started 479 and recording of the circular buffer 443 to a second data storage device is initiated; and if recording is already activated (as determined at step 473), the TDT clock is reset and restarted, at step 481.

Figure 8:
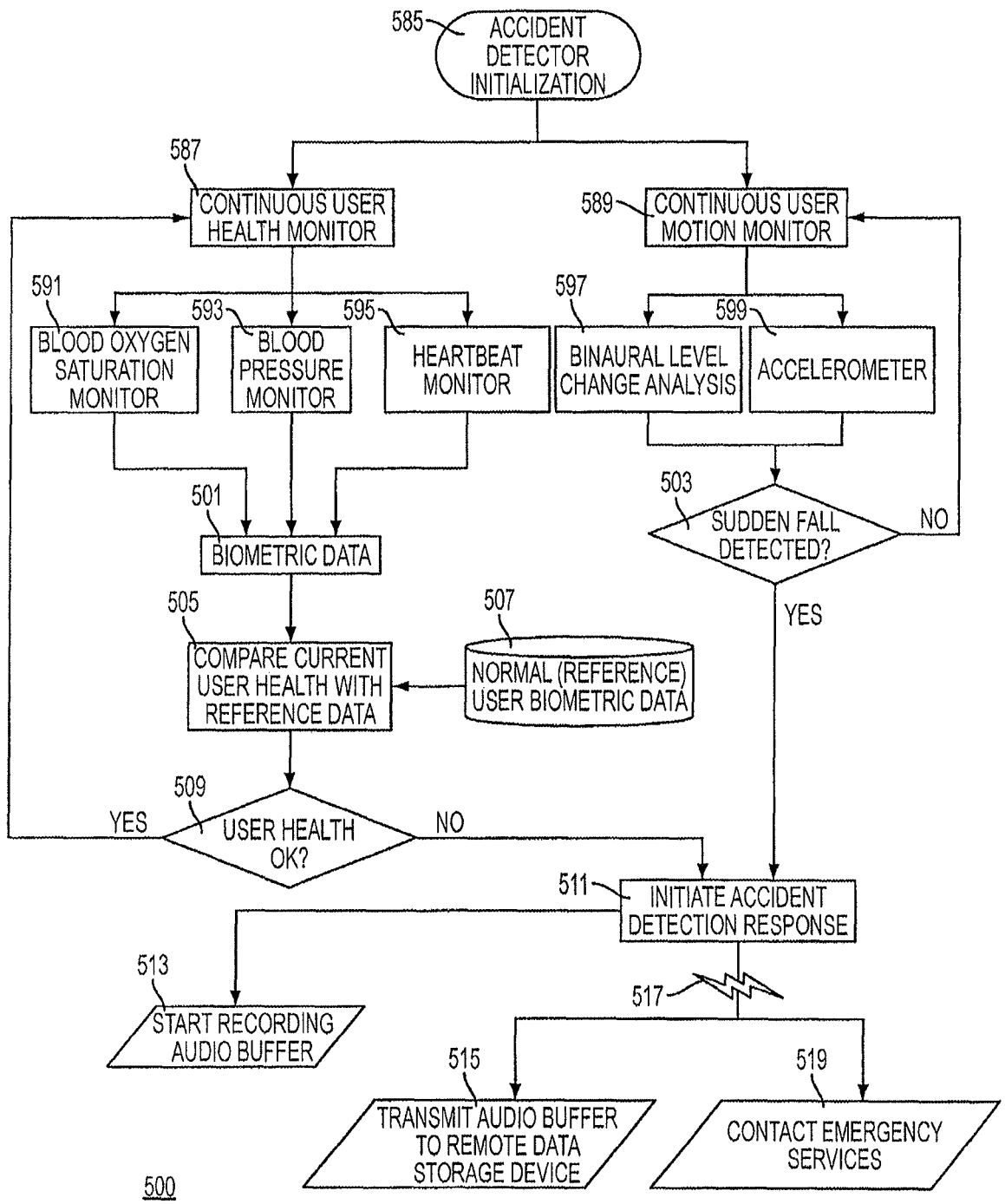
FIG. 8 is a flowchart of a method for event detection in accordance with at least one exemplary embodiment.

FIG. 8 is a flowchart of a method 500 for event detection in accordance with an exemplary embodiment. The method 500 can include more or less than the number of steps shown and is not limited to the order of the steps. To describe the method 500, reference will be made to components of FIG. 2, although it is understood that the method 500 can be implemented in any other manner using other suitable components. The method 500 can be implemented in a single earpiece, a pair of earpieces, headphones, or other suitable headset audio delivery device.

In one embodiment, the method 500 describes an accident detection platform, with the purpose of recording the audio signals selected in the system 300 process in FIG. 4 in response to a detected accident involving an AOBRS user. Following activation of accident detection 585, aspects of both the User's health 587 and physical motion 589 can be simultaneously and continuously monitored. Aspects of user health may include (but are not limited to) blood oxygen saturation 591, blood pressure 593 and heart-rate 595. These health aspects may be monitored using a probe mounted on the earphone device. The resulting biometric data 501 is compared SOS with a set of reference (normal, healthy) data 507, which may be from a database adapted to the particular user, or from a database generalized for users of a similar age, sex etc. If the comparison SOS of current biometric data 501 and reference data 507 indicates a sudden discrepancy, such as a drop in blood pressure 593, then decision unit 509 initiates a specific response 511. The user motion sensor system 589 monitors the location of the user using either of or a combination of analysis of the sound level at each earphone 597 using the output of the ASMs 403, 404 in both the left and right earphone; and/or an analysis of the spatial acceleration of the earphone device using accelerometers 599 and or internal sensors housed within the earphone assembly. If either or both the motion sensors 597, 599 indicate a sudden movement indicative of a fall, then decision unit 503 initiates a specific response 511. Such specific responses include starting the binaural recording system 513, and transmitting selected audio signals (see FIG. 4) to a second data storage device 515, which may involve a wireless data communication system 517, and may automatically invoke a system to alert the emergency services of a detected accident involving the AOBRS user 519.

Figure 9:
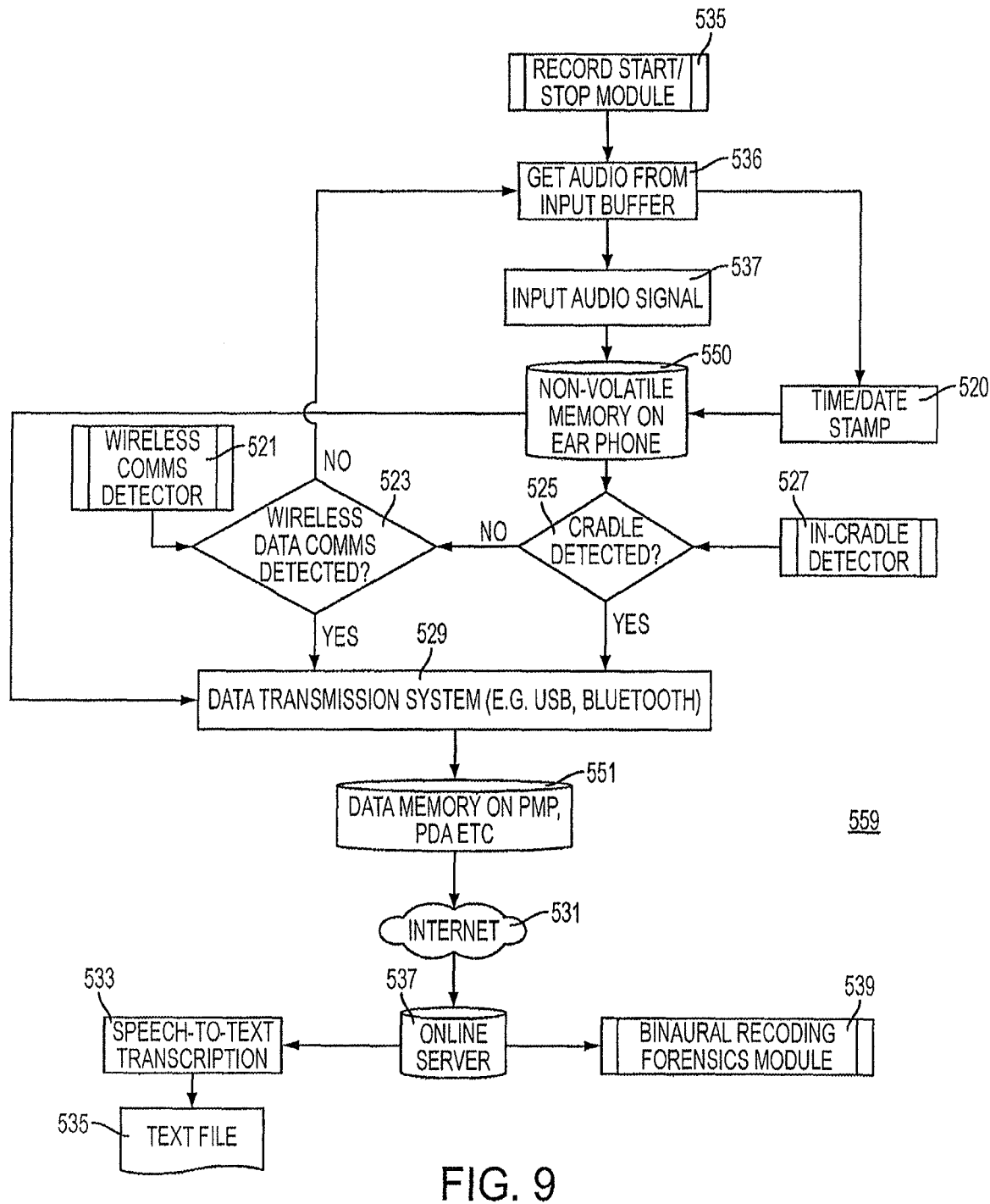
FIG. 9 is a flowchart of a method for forensic audio evaluation in accordance with at least one exemplary embodiment.

FIG. 9 is a flowchart of a method 559 for forensic audio evaluation in accordance with an exemplary embodiment. The method 559 can include more or less than the number of steps shown and is not limited to the order of the steps. To describe the method 559, reference will be made to components of FIG. 2, although it is understood that the method 559 can be implemented in any other manner using other suitable components. The method 559 can be implemented in a single earpiece, a pair of earpieces, headphones, or other suitable headset audio delivery device.

Method 559 describes an audio forensics system for transferring recording audio data 537 from memory on the earphone 550 or a second data storage system 551 to an online server 537 for analysis 539 (for example, via Internet 531), or automatic speech-to-text processing 533, 535. The recorded audio data 536, (responsive to record start/stop module 535), is time-stamped 520 to mark when the recording commenced, and time-stamps may be embedded in the recorded data stream at regular intervals or to mark significant events such as detected transient events (FIG. 7). Transmission of data 529 recorded on non-volatile memory in the earphone 550 to a second data system may be invoked automatically by decision unit 525 when an in-cradle detection system 527 detects that the earphones are located in a docking station (e.g. for recharging batteries). Alternatively, or additionally, transmission of data 529 recorded on non-volatile memory in the earphone 550 to a second data system 551 may be invoked automatically whenever the AOBRS detects 523 the presence of a wireless communication system 521, such as Wifi or Bluetooth.

Figure 10:
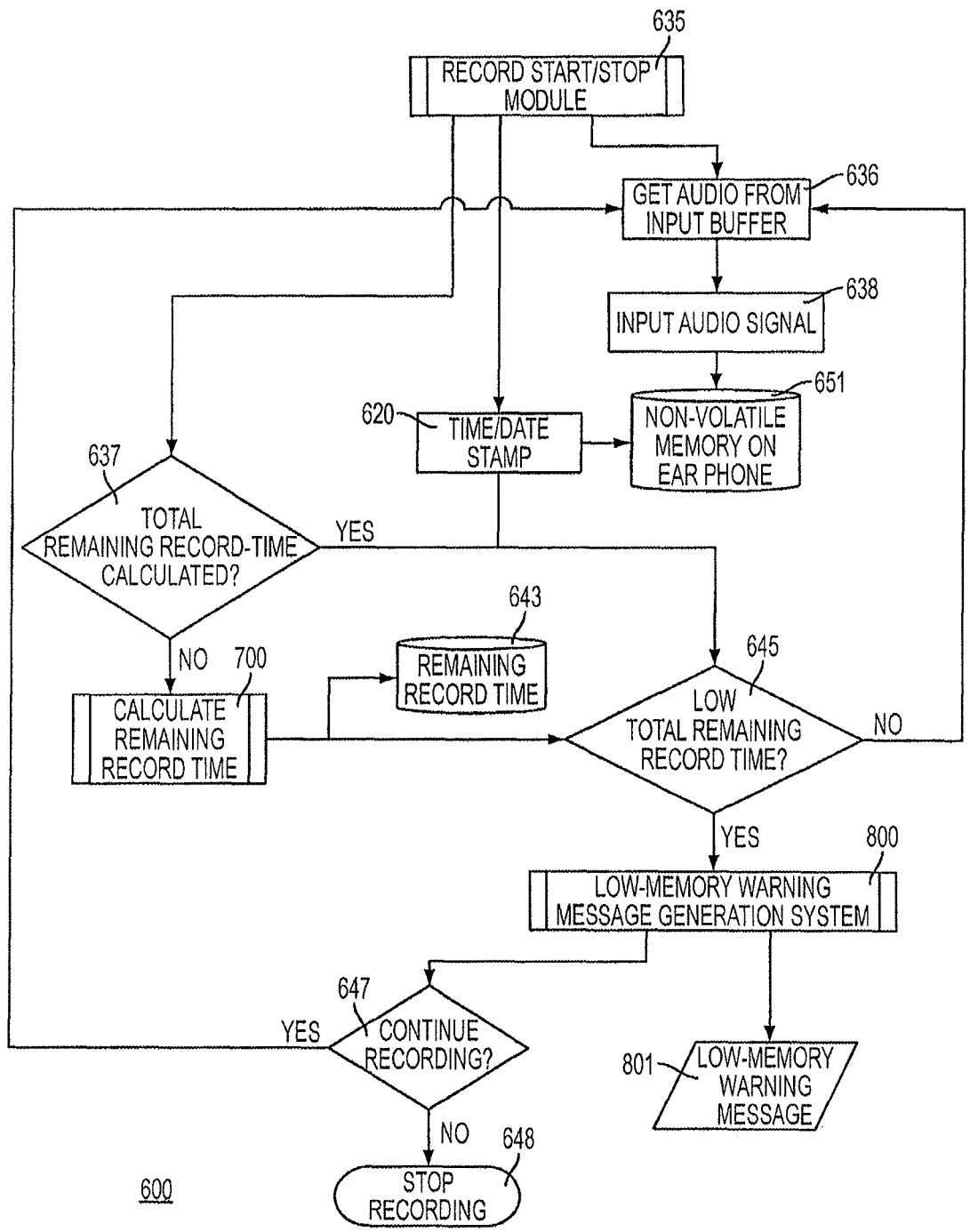
FIG. 10 is a flowchart of a method for low remaining-memory warning in accordance with at least one exemplary embodiment.

FIG. 10 is a flowchart of a method 600 for low remaining-memory warning in accordance with an exemplary embodiment. The method 600 can include more or less than the number of steps shown and is not limited to the order of the steps. To describe the method 600, reference will be made to components of FIG. 2, although it is understood that the method 600 can be implemented in any other manner using other suitable components. The method 600 can be implemented in a single earpiece, a pair of earpieces, headphones, or other suitable headset audio delivery device.

The method 600 can inform the user when the remaining data memory for storage of audio signals in the system 300 is critically low (similar to a low battery alarm). The record start/stop module 635 can get audio from the input buffer at step 636, and input the audio signal at step 638, to the non-volatile memory 208 on the earpiece 100 as shown in 651. A time stamp 620 can be included with the recorded audio signal.

During recording, the processor 121 at step 637 proceeds to determine if a total remaining record time is available. If the remaining record time is not available, the processor 121 can calculate it as shown in step 700 (see FIG. 11) and store the remaining record time to memory at step 643. At step 645 the processor 121 then determines if the total remaining record time is low. If the total record time is not low, the method proceeds back to step 636 to get the next audio from the input buffer. If however, the total record time is low, a low-memory warning message generation system 800 (see FIG. 12) generates a low memory warning message at step 801. Upon delivering the low-memory warning message, a determination is made at step 647 to continue recording. The recording can stop at step 648, for example, in response to a user request or automatic event detection. The method 600 can proceed back to step 636 to get the next audio data if the recording is continued.

Figure 11:
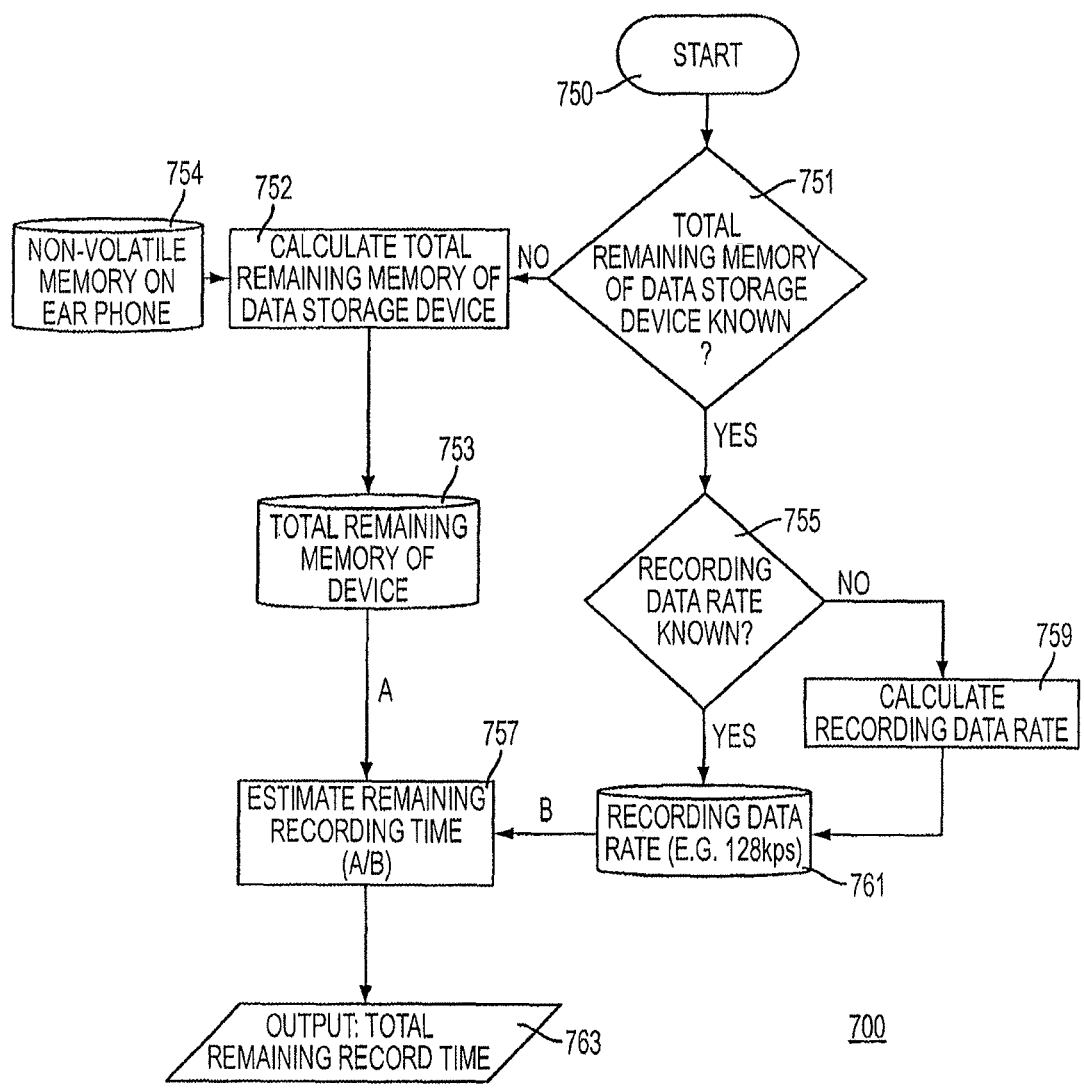
FIG. 11 is a flowchart of a method for remaining record-time in accordance with at least one exemplary embodiment.

FIG. 11 is a flowchart of a method 700 for remaining record-time in accordance with an exemplary embodiment. The method 700 can include more or less than the number of steps shown and is not limited to the order of the steps. To describe the method 700, reference will be made to components of FIG. 2, although it is understood that the method 700 can be implemented in any other manner using other suitable components. The method 700 can be implemented in a single earpiece, a pair of earpieces, headphones, or other suitable headset audio delivery device.

At step 750, the method 700 can start. At step 751, the processor 121 can determine if a total remaining memory of data storage of a device is known. If the total remaining memory is known, and the recording data rate is known at step 755, the data can be recorded at a designated recording rate as shown in step 761 based on the remaining memory and the data rate. If the recording rate is not known at step 755, the processor 121 can calculate the recording data rate at step 759 (e.g., 512 kps).

If however at step 751, the total remaining memory is not known, the processor 121 can calculate a total remaining memory of data storage at step 752 using the non-volatile memory on the earpiece 100 from step 754. At step 753, the total remaining memory of the device can be used in step 757 to estimate a remaining recording time (A/B). At step 763, the total remaining recording time can be output. For instance, upon the completion of method 700, the earpiece 100 can present a warning indication with the total remaining recording time left on the earpiece 100.

Figure 12:
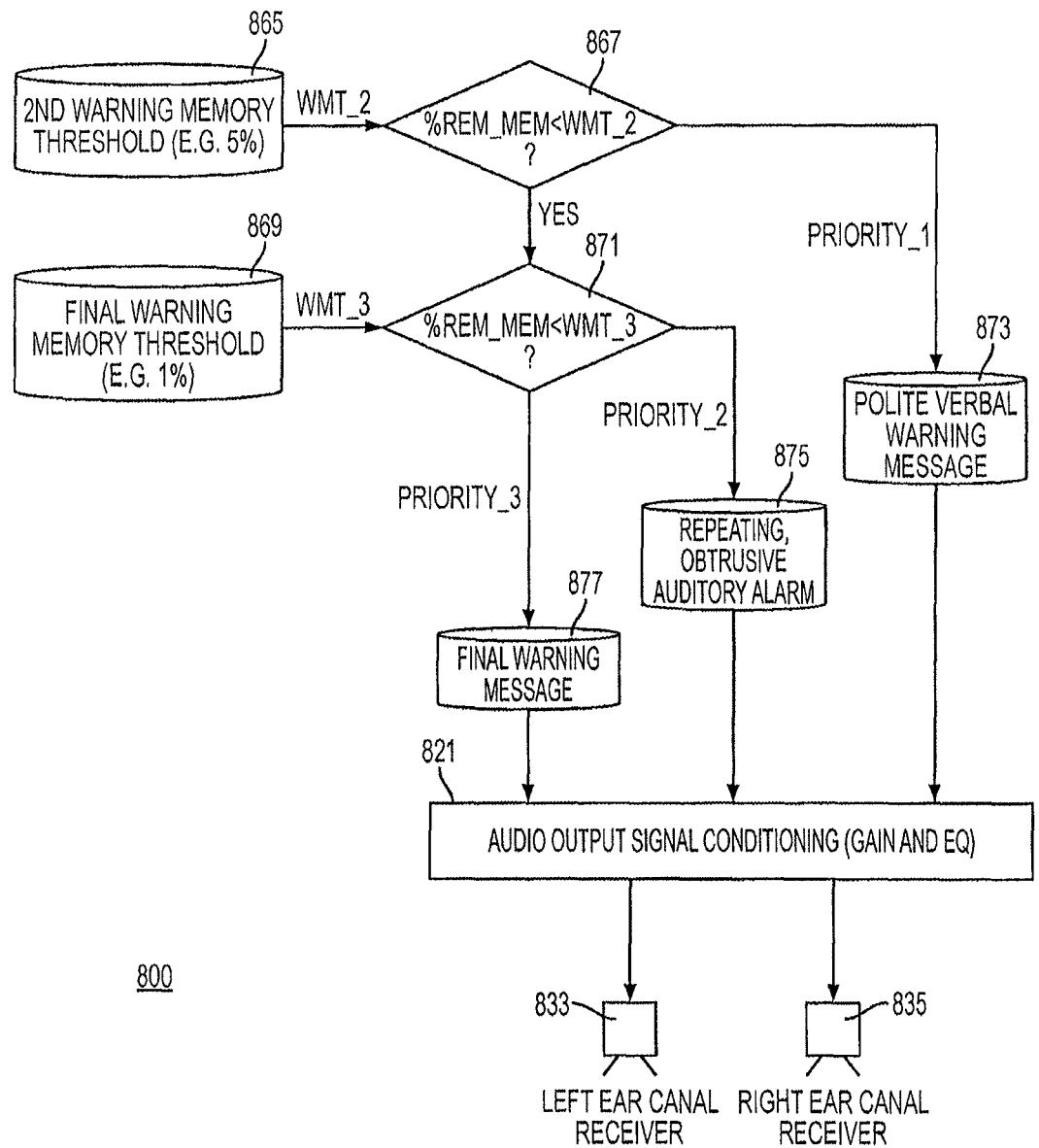
FIG. 12 is a flowchart of a method for remaining memory in accordance with at least one exemplary embodiment.

FIG. 12 is a flowchart of a method 800 for remaining memory in accordance with an exemplary embodiment. The method 800 can include more or less than the number of steps shown and is not limited to the order of the steps. To describe the method 800, reference will be made to components of FIG. 2, although it is understood that the method 800 can be implemented in any other manner using other suitable components. The method 800 can be implemented in a single earpiece, a pair of earpieces, headphones, or other suitable headset audio delivery device.

Briefly, method 800 prioritizes warning levels for reporting based on memory usage and remaining memory capacity. The method 800 can start when the "always-on" binaural recording feature is running on the earpiece 100. Notably, the memory 208 will be filled as recent portions of audio history are committed to the memory 208. The processor 121 can periodically check the memory capacity to determine when, and a type of warning message, to be sent to the user.

At step 867, the processor 121 can compare the remaining memory to a warning memory threshold (WMT_2) indicated in a database 865. For instance, the WMT_2 can be set to 5% remaining capacity. If the remaining memory is greater than the WMT_2 (>95% used capacity), the processor 121 can assign a priority level 1 and generate a polite verbal warning message to the user at step 873. The audio output of the warning message can be conditioned (e.g., gain, EQ) at step 821 and delivered to the user via the left ECR 833 and right ECR 835 of the earpiece. If however at step 871, the remaining memory is less than the WMT_2, but greater than a WMT_3, the processor 121 can assign a priority level 2 and generate a repeating warning message (obtrusive auditory alarm) audibly presented to the user as shown in step 875. If however at step 871, the remaining memory is less than a WMT_3 retrieved from data base 869, the processor 121 can assign a priority level 3 and generate a final verbal warning message to the user at step 877.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

I claim:

1. A system, comprising:
a processor; and
a sensor within an earpiece communicatively linked to the processor, wherein the processor performs operations comprising:
monitoring the orientation or location of a system or user based on an analysis of spatial acceleration of the earpiece using at least one of an accelerometer or GPS:
acquiring, by utilizing the sensor, biometric data associated with a user; comparing the biometric data with a set of reference data; detecting, based on the comparing, an event, wherein the event is detected based on a discrepancy resulting between the biometric data and the set of reference data, and wherein the event comprises at least one of a movement of a headset coupled to the processor, a touching of the headset, a tapping of the headset, a pressing of a button, a change in location of the earpiece, a recognizing of a voice command, a starting or ending of a call, or a combination thereof; and
initiating a response in response to the detecting of the event.

2. The system of claim 1, wherein the operations further comprise monitoring a location of
the user based on analyzing a sound level of an output of an ambient sound microphone of the earpiece.

3. The system of claim 1, wherein the response comprises initiating a binaural recording
system, transmitting a selected audio signal to a storage device, invoking a different system to alert an emergency service, or a combination thereof.

4. The system of claim 1, wherein the operations further comprise measuring ambient sound
occurring in an environment associated with the earpiece.

5. The system of claim 4, wherein the operations further comprise measuring internal sound
in an ear canal of the user.

6. The system of claim 5, wherein the operations further comprise continually recording a history of the ambient sound, the internal sound, or a combination thereof.

7. The system of claim 6, wherein the operations further comprise saving a recent portion of
the history in response to detecting the event.

8. The system of claim 7, wherein the operations further comprise compressing the recent
portion of the history in a memory of the system.

9. The system of claim 1, wherein the operations further comprise monitoring ambient sound for a sound pressure level change.

10. The system of claim 9, wherein the operations further comprise storing a history of
ambient sounds in a memory in response to detecting the sound pressure level change.

11. A system, comprising:
a processor; and
a sensor within an earpiece communicatively linked to the processor, wherein the processor performs operations comprising:
acquiring, by utilizing the sensor, biometric data associated with a user;
comparing the biometric data with a set of reference data;
detecting, based on the comparing, an event, wherein the event is detected based on a discrepancy resulting between the biometric data and the set of reference data, and wherein the event comprises at least one of a movement of a headset coupled to the processor, a touching of the headset, a change in location of the earpiece, a recognizing of a voice command, a starting or ending of a call, or a combination thereof; and
initiating a response in response to the detecting of the event,
wherein the operations further comprise monitoring a location of the user based on an analysis of spatial acceleration of the earpiece.

12. A system, comprising:
a processor; and
a sensor within an earpiece communicatively linked to the processor, wherein the processor performs operations comprising:
acquiring, by utilizing the sensor, biometric data associated with a user;
comparing the biometric data with a set of reference data;
detecting, based on the comparing, an event, wherein the event is detected based on a discrepancy resulting between the biometric data and the set of reference data, and wherein the event comprises a movement of a headset coupled to the processor, a touching of the headset, a change in location of the earpiece, a recognizing of a voice command, a starting or ending of a call, or a combination thereof; and
initiating a response in response to the detecting of the event, wherein the operations further comprise measuring ambient sound occurring in an environment associated with the earpiece, wherein the operations further comprise measuring internal sound in an ear canal of the user, wherein the operations further comprise continually recording a history of the ambient sound, the internal sound, or a combination thereof, wherein the operations further comprise saving a recent portion of the history in response to detecting the event, wherein the operations further comprise compressing the recent portion of the history in a memory of the system, and wherein the operations further comprise issuing a warning message to inform the user when a remaining memory receiving the recent portion of the history is below a predetermined value.

13. A method, comprising:
obtaining, from a sensor of an earpiece and by utilizing a processor communicatively coupled to the sensor, biometric data associated with a user;
monitoring the orientation or location of the earpiece using at least one of an accelerometer or GPS;
obtaining, from a microphone of the earpiece and by utilizing the processor communicatively coupled to the microphone, voice data from the user;
comparing the biometric data with a set of reference data;
comparing the voice data with a set of reference voice data;
detecting, based on the comparing, an event, wherein the event is detected based on a discrepancy resulting between the biometric data and the set of reference data or the voice data and set of reference voice data, and wherein the event comprises at least one of a movement of a headset coupled to the processor, a touching of the headset, tapping a portion of the earpiece, pressing a button, a change in location of the earpiece, a recognizing of a voice command, a starting or ending of a call, decreased heart rate, increased heart rate, blood oxygen saturation, blood pressure, or a combination thereof; and
generating a response in response to the detecting of the event.

14. The method of claim 13, further comprising saving a history of ambient sound, internal sound, audio content, or a combination thereof in a buffer.

15. The method of claim 14, further comprising applying a compression technique to data in the buffer to reduce a dimensionality of the data.

16. The method of claim 15, further comprising streaming the compressed data from an audio interface.

17. The method of claim 13, further comprising recording the location of the earpiece at a time of the event.

18. The method of claim 13, further comprising tagging data held in a memory of the earpiece with a filename or header that reflects a condition associated with the event.

19. The method of claim 13, further comprising receiving a request to retrieve audio data from the earpiece.

20. An earpiece, comprising:
a sensor communicatively linked to a processor, wherein the processor performs operations comprising:
monitoring the orientation or location of a system or user based on an analysis of spatial acceleration of the earpiece using at least one of an accelerometer or GPS:
acquiring, by utilizing the sensor, biometric data associated with the user;
comparing the biometric data with a set of reference data;
detecting, based on the comparing, an event, wherein the event is detected based on a discrepancy resulting between the biometric data and the set of reference data, and wherein the event comprises a drop in blood oxygen saturation, an elevation of blood oxygen saturation, a drop of heart rate, an elevation of heart rate, elevated breathing rate, and reduced breathing rate, or a combination thereof; and
generating a response in response to the detecting of the event, where a response includes sending a message wirelessly to a remote server.

* * * * *

UNITED STATES PATENT AND TRADEMARK OFFICE
CERTIFICATE OF CORRECTION

PATENT NO. : 10,616,702 B2
APPLICATION NO. : 16/260454
DATED : April 7, 2020
INVENTOR(S) : Steven W. Goldstein It is certified that error appears in the above-identified patent and that said Letters Patent is hereby corrected as shown below:

On the Title Page

Item (12) delete "Goldstein" and insert --Goldstein et al.--

Item (72) Inventors should read:
--(72) Inventors: Steven W. Goldstein, Delray Beach, FLORIDA (US);
John Usher, Devon (GB);
Marc Andre Boillot, Plantation, FLORIDA (US)--

Signed and Sealed this
Seventh Day of February, 2023

Katherine Kelly Vidal
*Director of the United States Patent and Trademark Office*